United States Patent
Barciszewski et al.

(10) Patent No.: US 8,404,660 B2
(45) Date of Patent: Mar. 26, 2013

(54) METHOD OF OBTAINING OF 4-N-FURFURYLCYTOSINE AND/OR ITS DERIVATIVES, AN ANTI-AGING COMPOSITION AND USE OF 4-N-FURFURYLCYTOSINE AND/OR ITS DERIVATIVES IN THE MANUFACTURE OF ANTI-AGING COMPOSITION

(75) Inventors: Jan Barciszewski, Poznan (PL); Wojciech T. Markiewicz, Poznan (PL); Eliza Wyszko, Poznan (PL); Maria Markiewicz, Poznan (PL); Monika Nowak, Kostrzyn (PL); Katarzyna Rolle, Kamionki (PL); Ewelina Adamska, Kamien Pomorski (PL); Marcin K. Chmielewski, Poznan (PL)

(73) Assignee: Instytut Chemii Bioorganicznej Pan, Poznan (PL)

( * ) Notice: Subject to any disclaimer, the term of this patent is extended or adjusted under 35 U.S.C. 154(b) by 315 days.

(21) Appl. No.: 12/744,349

(22) PCT Filed: Nov. 25, 2008

(86) PCT No.: PCT/PL2008/000089
§ 371 (c)(1),
(2), (4) Date: Aug. 2, 2010

(87) PCT Pub. No.: WO2009/067035
PCT Pub. Date: May 28, 2009

(65) Prior Publication Data
US 2010/0317612 A1 Dec. 16, 2010

(30) Foreign Application Priority Data
Nov. 25, 2007 (PL) .................................. 383867

(51) Int. Cl.
*A01N 43/04* (2006.01)
*A61K 31/70* (2006.01)
(52) U.S. Cl. .......................................... 514/49; 514/43
(58) Field of Classification Search ........................ None
See application file for complete search history.

(56) References Cited

U.S. PATENT DOCUMENTS

| | | | |
|---|---|---|---|
| 4,753,948 | A | 6/1988 | Szantay |
| 5,151,425 | A | 9/1992 | Clark |
| 2009/0023672 | A1 | 1/2009 | Inoue et al. |

FOREIGN PATENT DOCUMENTS

| | | |
|---|---|---|
| CA | 2107896 A1 | 11/1992 |
| CA | 1339503 C | 10/1997 |
| DE | 4323615 A1 | 1/1995 |
| JP | 2000319184 A | 11/2000 |
| JP | 2001031549 | 2/2001 |
| JP | 2001031549 A | 2/2001 |
| KR | 20010001290 A | 1/2001 |
| WO | WO9220340 A1 | 11/1992 |
| WO | 00/31102 A | 6/2000 |
| WO | 2005/020885 A | 3/2005 |
| WO | 2006080262 A1 | 8/2006 |

OTHER PUBLICATIONS

Anderson, E., et al.: "The Synthesis of Diene-Containing Nucleoside Phosphoramidites and their Use in the Labeling of Oligonucleotides", Nucleosides, Nucleotides and Nucleic Acids, Taylor & Francis, Philadelphia, PA, vol. 24, No. 5/7, Jan. 1, 2005, pp. 761 to 765, XP008104495.
Curran, W.V., et al.: "Some New Syntheses of Amino-and Alkylaminopyrimidines and -pteridines", Journal of Organic Chemistry, vol. 28, No. 10, 1963, pp. 2672 to 2677, XP002525818.
Database Registry [Online], Chemical Abstracts Service, Columbus, Ohio, U.S., Mar. 23, 2005, XP002525819.
Pola Chem Ind Inc , "Agents for reconstituting dermal collagen fasciculus, useful in cosmetics, contains an adenine derivative", Database, WPI Week 2001 Nr. 33, Thomson Scientific, London, GB; AN 2001-310476, XP002539227.

*Primary Examiner* — Patrick Lewis
(74) *Attorney, Agent, or Firm* — Christopher L. Parmelee; Walker & Jocke (57) ABSTRACT

The subjects of the present invention are the method of preparation of 4-furfurylcytosine and/or its derivatives, its use in the manufacture of anti-aging compositions and an anti-aging composition. As 4-furfurylcytosine and/or its derivatives possesses a series of biological properties it might be use as a composition having excellent anti-aging effect to prevent the sagging of skin and loss of luster and to improve sufficiently its aesthetic appearance without significantly change the growth rate and the total growth ability of the skin. Optimal methods of manufacturing this compound, while at the same time obtaining the highest possible process efficiency, with particular emphasis on its utility in the pharmaceutical and cosmetic industries are presented.

7 Claims, 6 Drawing Sheets

```
                        SEQUENCE LISTING

<160> NUMBER OF SEQ ID NOS: 2

<210> SEQ ID NO 1
<211> LENGTH: 19
<212> TYPE: DNA
<213> ORGANISM: artificial
<220> FEATURE:
<223> OTHER INFORMATION: synthetic oligonucleotide

<400> SEQUENCE: 1
gggtggagcc aaacgggtc                                            19

<210> SEQ ID NO 2
<211> LENGTH: 21
<212> TYPE: DNA
<213> ORGANISM: artificial
<220> FEATURE:
<223> OTHER INFORMATION: synthetic oligonucleotide

<400> SEQUENCE: 2
ggagttgctg ttgaagtcgc a                                         21
```

METHOD OF OBTAINING OF 4-N-FURFURYLCYTOSINE AND/OR ITS DERIVATIVES, AN ANTI-AGING COMPOSITION AND USE OF 4-N-FURFURYLCYTOSINE AND/OR ITS DERIVATIVES IN THE MANUFACTURE OF ANTI-AGING COMPOSITION

The subjects of the present invention are: the method of obtaining of 4-furfurylcytosine and/or its derivatives, an anti-aging composition and use of 4-furfurylcytosine and/or its derivatives in the manufacture of anti-aging compositions. As 4-furfurylcytosine and its derivatives possesses a series of biological properties it might be use as a composition having excellent anti-aging effect to prevent the sagging of skin and loss of luster and to improve sufficiently its aesthetic appearance without significantly change the growth rate and the total growth ability of the skin. Optimal methods of manufacturing this compound, while at the same time obtaining the highest possible process efficiency, with particular emphasis on its utility in the pharmaceutical and cosmetic industries are presented.

In patent descriptions JP2000319184 (publ. Nov. 21, 2000), WO9220340 (publ. Nov. 26, 1992) a method for improving aesthetic appearance of mammalian skin by applying a composition including an effective amount of a substituted aminopurine cytokinin to mammalian skin. A composition including an effective amount of 6-(substituted amino)purine cytokinin [for example, kinetin (6-furfurylaminopurine) or the like] is applied to mammalian skin in such an amount that can improve sufficiently its aesthetic appearance, but does not significantly change the growth rate and the total growth ability of the skin.

In patent descriptions CA2107896 (publ. Nov. 17, 1992), CA1339503 (publ. Oct. 21, 1997) a method and composition for treating hyperproliferative skin diseases using 6-aminopurine cytokinins are described. It has been discovered that 6-(substituted amino)purine cytokinins, such as kinetin, induce differentiation, and consequently reduce or eliminate the abnormally high rate of proliferation, of hyperproliferating associated with hyperproliferative skin diseases, such as psoriasis. Thus, the present invention provides methods and compositions for treating hyperproliferative skin diseases in mammals, particularly such diseases associated with hyperproliferating epidermal cells in humans, by administering to the hyperproliferating cells associated with such a disease, in the skin of a mammal suffering from, a differentiation-inducing effective amount of a 6-(substituted amino)purine cytokinin.

In the patent description U.S. Pat. No. 5,151,425 (publ. Sep. 29, 1992) a method of and composition for treating inflammation and the immunological response thereto were described. The plant cytokinins are effective to treat the inflammation, to accelerate healing of lesions, and to provide substantially immediate relief of pain, itching, and other immunological responses resulting from inflammation. The plant cytokinin is administered to the mammal in a suitable pharmaceutical preparation. A composition for topical use in accordance with the method comprises an effective amount of the plant cytokinin in a carrier suitable for topical application to the human skin, for example, hydrophilic ointment, isopropyl alcohol, or a powder formulation.

In the patent application WO2006080262 (publ. Aug. 3, 2006) an AGE-2 aptamer was described. An AGE-2 aptamer binds to advanced glycation end-product (AGE-2) originating in glyceraldehyde but not to human serum albumin and comprises at least 35 bases and in which the cytosine content in the bases thereof is at least 35% or the guanine content in the bases thereof is at least 32%.

In the patent application KR20010001290 (publ. Jan. 5, 2001) composition for external use showing improvement effect on skin wrinkle and inhibition effect on wrinkle-formation were described. A composition for external use containing retinoid, vegetable sterol, isoflavonoid, cytokinin and glycyrrhetic acid is provided, which improves skin wrinkle and shows good inhibition effect on wrinkle-formation.

In the patent application JP2001031549 (publ. Feb. 6, 2001) an agent for reconstructing dermal collagen fiber bundle and cosmetic containing the same were described. The compound may be extracted from a plant or synthesized from adenine and so on as raw materials. When the reconstructing agent is used for skin preparations for external use, the content of the reconstructing agent is preferably 0.001 to 5 wt. %, especially preferably 0.005 to 1 wt. %.

In the patent application U.S. Pat. No. 4,753,948 (publ. Jun. 28, 1988) a furfuryl derivatives of vinblastine-type bis-indoles, and pharmaceutical compositions containing them were described. The invention relates to novel furfuryl derivatives of the general formula (I), (I) wherein R1 stands for a hydrogen atom or an acetyl group, R2 stands for a hydroxyl or ethyl group of beta-position; R3 means an ethyl group of alpha-position; R4 represents a hydrogen atom; or R3 and R4 together represent an oxygen bridge; and B stands for a hydroxyl of an O-acyl group, as well as their acid addition salts and pharmaceutical preparations containing these compounds. Further on, the invention relates to a process for preparing these compounds and preparations. The compounds of the general formula (I) show a cytostatic activity with less toxicity than that of the commercially available known vinblastine-type bis-indole alkaloid drugs.

Despite the above described compounds, compositions and methods of manufacturing such compositions for external use showing improvement effect on skin wrinkle and inhibition effect on wrinkle-formation, compositions including cytokinins, substituted cytokinins and novel furfuryl derivatives which applied to mammalian skin in such an amount that can improve sufficiently its aesthetic appearance, there is still a need to obtain an optimal method of manufacturing compounds which show a cytostatic activity with less toxicity, used for skin preparations.

The goal of the present invention is to provide a method which may be used to manufacture 4-furfurylcytosine and/or its derivatives facilitating its further use in the cosmetic and pharmaceutical industries and the use of this compound as an anti-aging preparation, to obtain an external composition for skin having excellent antiaging effect to prevent the sagging of skin and loss of luster. The embodiment of such a stated goal and the solution of problems dealing with the antiaging compositions, which may be utilized in the manufacture of anti-aging compositions and which applied to mammalian skin in such an amount that can improve sufficiently its aesthetic appearance, does not significantly change the growth rate and the total growth ability of the skin, have been achieved in the present invention.

The subject of the present invention is a method of obtaining 4-N-furfurylcytosine and/or its derivatives, characterised in that the production of 4-N-furfurylcytosine and/or its derivatives, of the general formula wherein:

$R_1$, $R_2$, $R_3$=H lub alkyl, alkenyl, alkinyl, hydroxyalkyl or aryl $R_4$, $R_5$, $R_6$=H or alkyl $R_7$, $R_8$=H, $CH_3$, alkyl, alkenyl, alkinyl, hydroxyalkyl $R_9$=H, D-2-deoxyriboside, D-riboside, tetrahydropyranyl, wherein a method encompasses a reaction stage in which an aqueous solution of cytosine is supplemented with furfurylamines and a catalyst, preferentially ammonium chloride, whereafter the mixture is brought to boiling for 48 to 96 hours, cooled and extracted with dichloromethane, whereafter the organic phase is filtered in order to isolate the product and the raw product is then crystallised.

Preferentially, the molar ratio of cytosine characterised in that the molar ratio of cytosine to furfurylamine to the catalyst, ammonium chloride is 0.36:6:0.3.

Preferentially, the synthesis of 4-N-furfurylcytosine and/or its derivatives consists of three stages, where during the first stage 4-N-p-toluenesulfonyl-2'-deoxycytidine is synthesized, during the second stage the furfurylamine reacts with the 4-N-p-tosyl-2'-deoxycytidine, and the third stage consists of the formation of 4-N-furfurylcytosine and/or its derivatives through the degradation of the N-glycoside bond with an aqueous solution of an inorganic acid; following the formation of 4-N-furfurylcytosine and/or its derivatives, the acid if evaporated off or neutralised with aqueous sodium hydroxide, and the salt formed is separated on a chromatography column and the chromatographic purification is performed at least twice, where the chief product is eluted with an aqueous solution of methanol and the 4-N-furfurylcytosine is crystallized in water and colourless, needle-shaped crystals are obtained.

Preferentially, the degradation of the N-glycoside bond during the third stage is performed using an aqueous solution of an inorganic acid at a pH of 3-3.5, where the salt formed is separated on a chromatography column at a temperature of 40-45° C., and the main product is eluted with a 0.1% aqueous solution of methanol.

Preferentially, reaction efficiency exceeds 85%.

Figure 1:
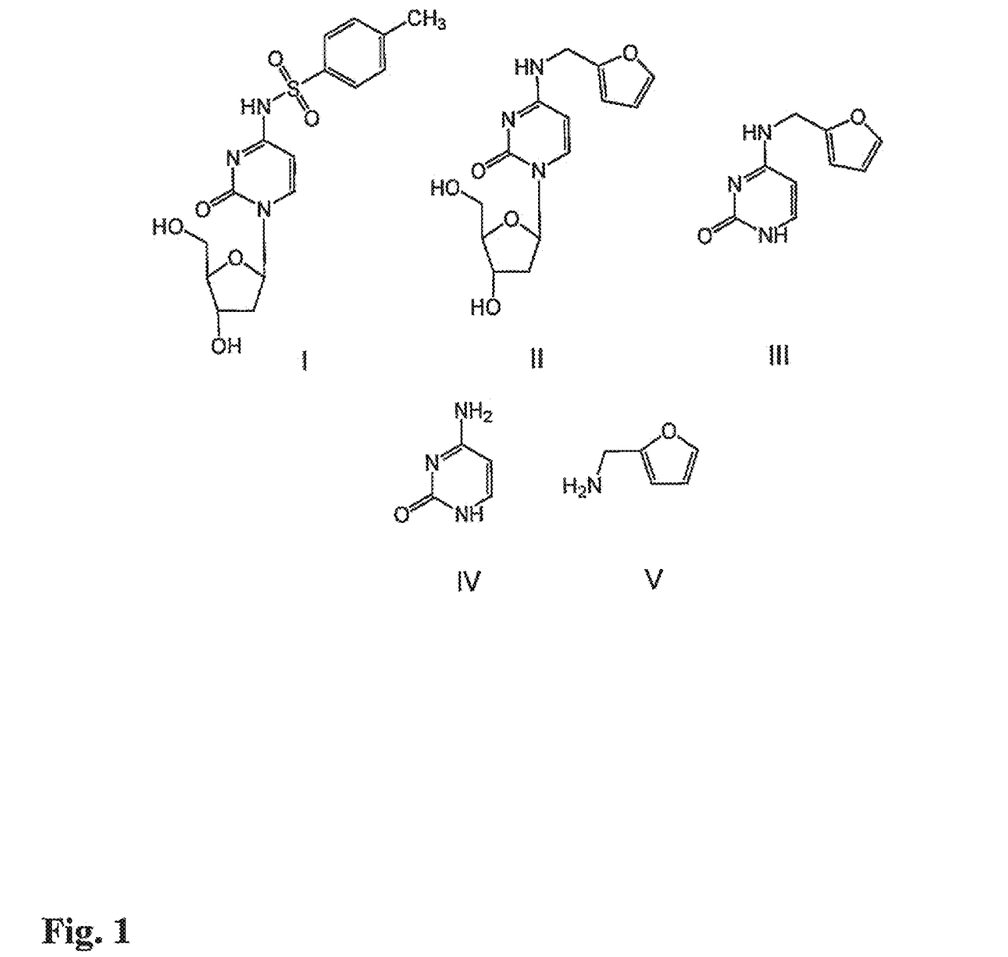

Preferentially, a method is presented in FIG. 1.

The next subject of invention is an anti-aging composition, characterised in that it contains 4-N-furfurylcytosine and/or its derivatives, of the general formula wherein:

$R_1$, $R_2$, $R_3$=H lub alkyl, alkenyl, alkinyl, hydroxyalkyl or aryl $R_4$, $R_5$, $R_6$=H or alkyl $R_7$, $R_8$=H, $CH_3$, alkyl, alkenyl, alkinyl, hydroxyalkyl $R_9$=H, D-2-deoxyriboside, D-riboside, tetrahydropyranyl.

Preferentially, the 4-N-furfurylcytosine and/or its derivatives content in the composition is up to 2%.

Preferentially, the composition contains 4-N-furfurylcytosine and/or its derivatives the synthesis of which encompasses a reaction stage in which an aqueous solution of cytosine is supplemented with furfurylamines and a catalyst, preferentially ammonium chloride, whereafter the mixture is brought to boiling for 48 to 96 hours, cooled and extracted with dichloromethane, whereafter the organic phase is filtered in order to isolate the product and the raw product is then crystallised.

Preferentially, the composition contains 4-N-furfurylcytosine and/or its derivatives obtained through the production of 4-N-furfurylcytosine and/or its derivatives, where the molar ratio of cytosine to furfurylamine to the catalyst, ammonium chloride is 0.36:6:0.3.

Preferentially, the composition contains 4-N-furfurylcytosine and/or its derivatives the synthesis of which consists of three stages, where during the first stage 4-N-p-toluenesulfonyl-2'-deoxycytidine is synthesized, during the second stage the furfurylamine reacts with the 4-N-p-tosyl-2'-deoxycytidine, and the third stage consists of the formation of 4-N-furfurylcytosine and/or its derivatives through the degradation of the N-glycoside bond with an aqueous solution of an inorganic acid; following the formation of 4-N-furfurylcytosine and/or its derivatives, the acid if evaporated off or neutralised with aqueous sodium hydroxide, and the salt formed is separated on a chromatography column and the chromatographic purification is performed at least twice, where the chief product is eluted with an aqueous solution of methanol and the 4-N-furfurylcytosine is crystallized in water and colourless, needle-shaped crystals are obtained.

Preferentially, the degradation of the N-glycoside bond during the third stage is performed using an aqueous solution of an inorganic acid at a pH of 3-3.5, where the salt formed is separated on a chromatography column at a temperature of 40-45° C., and the main product is eluted with a 0.1% aqueous solution of methanol.

The next subject of invention is use of 4-N-furfurylcytosine and/or its derivatives, of a general formula wherein:

$R_1$, $R_2$, $R_3$=H lub alkyl, alkenyl, alkinyl, hydroxyalkyl or aryl $R_4$, $R_5$, $R_6$=H or alkyl $R_7$, $R_8$=H, $CH_3$, alkyl, alkenyl, alkinyl, hydroxyalkyl $R_9$=H, D-2-deoxyriboside, D-riboside, tetrahydropyranyl, in the production of anti-aging compositions.

Preferentially, the 4-N-furfurylcytosine and/or its derivatives content in the anti-aging preparation is up to 2%.

Preferentially, the 4-N-furfurylcytosine and/or its derivatives is obtained in a reaction stage in which an aqueous solution of cytosine is supplemented with furfurylamines and a catalyst, preferentially ammonium chloride, whereafter the mixture is brought to boiling for 48 to 96 hours, cooled and extracted with dichloromethane, whereafter the organic phase is filtered in order to isolate the product and the raw product is then crystallised.

Preferentially, the 4-N-furfurylcytosine and/or its derivatives is obtained through the production of 4-N-furfurylcytosine and/or its derivatives, where the molar ratio of cytosine to furfurylamine to the catalyst, ammonium chloride is 0.36:6:0.3.

Preferentially, the synthesis of 4-N-furfurylcytosine and/or its derivatives consists of three stages, where during the first stage 4-N-p-toluenosulfonyl-2'-deoxycytidine is synthesized, during the second stage the furfurylamine reacts with the 4-N-p-tosyl-2'-deoxycytidine, and the third stage consists of the formation of 4-N-furfurylcytosine and/or its derivatives through the degradation of the N-glycoside bond with an aqueous solution of an inorganic acid; following the formation of 4-N-furfurylcytosine and/or its derivatives, the acid if evaporated off or neutralised with aqueous sodium hydroxide, and the salt formed is separated on a chromatography column and the chromatographic purification is performed at least twice, where the chief product is eluted with an aqueous solution of methanol and the 4-N-furfurylcytosine is crystallized in water and colourless, needle-shaped crystals are obtained.

Preferentially, the degradation of the N-glycoside bond during the third stage is performed using an aqueous solution of an inorganic acid at a pH of 3-3.5, where the salt formed is separated on a chromatography column at a temperature of 40-45° C., and the main product is eluted with a 0.1% aqueous solution of methanol.

The attached figures facilitate a better explanation of the nature of the present invention.

FIG. 1 presents the described synthesis of 4-N-furfurylcytosine, where:

(I) 4-N-p-toluensulfonyl-2'-deoxycytydine, (II) 4-N-furfuryl-2'-deoxycytidine, (III) 4-N-furfurylcytosine, (IV) cytosine and (a) furfurylamine (V), (5 equiv.) in pyridine, 80° C., 24 h; (b) 1M aqueous HCl, 100° C., 0.5 h.

FIG. 2 presents a cytotoxicity analysis of furfurylcytosine (FC) in fibroblast cells cultured from 1 day to 5 weeks.

A. Images of fibroblast cells treated with 100 μM furfurylcytosine towards untreated control (C). Cells were checked after 1 day-5 weeks.

B. RT-PCR analysis of GAPDH cDNA expression in fibroblast cells cultured 5 weeks in presence of 100 μM FC towards untreated control. Total RNA was isolated from living cells for RT reaction. PCR was done with specific primers. 300 bp fragments were separated on 1% agarose stained with ethidium bromide.

C. Graph showing percentage participation of GAPDH cDNA expression effected FC. 100% GAPDH expression was estimated for control cells. Differences in expression level was determined using Phosphoimager and ImageQant program.

A. Images of Hela cells cultured during 24 hours treated with 100 μM FC towards untreated.

B. RT-PCR analysis of DNMT-1 (500 bp) gene expression in HeLa cells treated with FC towards untreated. Analysis of GAPDH (300 bp) gene expression was performed as a internal control. DNA fragments were separated on 1% agarose gel stained with ethidium bromide.

FIG. 5 presents the general structure of furfurylcytosine, wherein $R_1=R_2=R_3=R_4=R_5=R_6=R_7=R_8=R_9$=H) and its derivatives, wherein:

$R_1$, $R_2$, $R_3$=H or alkyl, alkenyl, alkinyl, hydroxyalkyl or aryl $R_4$, $R_5$, $R_6$=H or alkyl $R_7$, $R_8$=H, $CH_3$, alkyl, alkenyl, alkinyl, hydroxyalkyl $R_9$=H, D-2-deoxyriboside, D-riboside, tetrahydropyranyl Below, there are example embodiments of the present invention defined above.

EXAMPLES

All the solvents used in the reactions were purified and dried according to the standard procedures. In the reactions commonly available reagents were used: trimethylsilyl chloride—TMSCI (POCh, Poland), p-toluenosulfonyl chloride (Fluka), concentrated aqueous ammonia (Merck), furfurylamine (Fluka). Thin layer chromatography (TLC) was performed on plates of Silicagel 60 $F_{254}$ (Merck), where the following solvent system was applied: (A) dichloromethane/methanol (8:2) as eluent. To detect the UV-absorbance shortwave ultraviolet light (254 nm) was used. The column chromatography separation was carried out on the reverse silica gel 60 silanised 0.063-0.200 mm (Merck) in the following eluent: warm water/methanol (99.9:0.1). $^1$H-NMR and $^{13}$C-NMR spectra were recorded using a Varian 300 MHz spectrometer DMSO and DMSO with $D_2O$ were used as solvent. Mass spectra (EMS) were measured with ES-MS Micromass ZQ (Waters).

Example 1

The Chemical Synthesis of 4-N-furfurylcytosine in Three Steps

The chemical synthesis of 4-N-furfurylcytosine was achieved in three steps (FIG. 1). The first step was the synthesis of 4-N-p-toluenosulfonyl-2'-deoxycytidine (FIG. 1 I) which was carried out according to the former procedure described by Markiewicz et al. [Markiewicz W. T., Gröger G., Rösch R., Zebrowska A., Markiewicz M., Klotz M., Godzina P. and Seliger H. "New method of synthesis of fluorescently labelled oligonucleotides and their application in DNA sequencing" (1997) Nucleic Acid Res., 25, 18, 3672-3680].

The second step was the reaction of furfurylamine (FIG. 1 V) with 4-N-p-toluenesulfonyl-2'-deoxycytidine (FIG. 1 I). The third step was depended on creating of 4-N-furfurylcytosine (FIG. 1 III), by cleavage of N-glycosyl bond by solution of inorganic acid in water (pH of this solution was about 3). When the reaction ended (what confirmed the dark yellow colour of the reaction mixture, the acid was evaporated or neutralised by water solution of sodium hydroxide where the received salt was lost on reverse column. The major product has shown low solubility in all solvents, but the best solubility was observed in water, and increased with temperature. In this reason, purity on the column was performed in warm water (40-45° C.). The column was referred by aluminum foil, because the decrease temperature of water was carried out to precipitate of the product on the gel. The purification of product was performed two times, because acid degradation of ribose gave a lot of byproducts, obstructed purification.

The main product was eluted in 0.1% warm water solution of methanol. When the temperature of solvent was higher than 45° C., the product could elute earlier. The 4-N-furfurylcytosine was crystallized in water, gave colorless crystals, which form thin needles.

To solution of 4-N-p-toluenesulfonyl-2'-deoxycytidine, (1.098; 2.878 mmol) in anhydrous pyridine (5.7 ml) furfurylamine (1.3 ml; 14 mmol) was added. The reaction flask was closed and kept in a drier at 80° C. for 12 hours. Next, to the mixture dichloromethane (15 ml) was added and all was extracted with water (3×15 ml). The water layer (with product) was evaporated under reduced pressure. White foam was obtained with yield 85%. The TLC analysis showed that it was a complete reaction: $R_f(A)$ 0.61.

$^1$H NMR (300 MHz, DMSO) δ 1.9 (m, 1H, H-2'); 2.0 (m, 1H, H-2"); 3.5 (d, J=2.4 Hz, 2H, H-5'); 3.7 (q, J=3.9 Hz, J=6.8 Hz, 1H, H-4'); 4.2 (q, J=3.16 Hz, J=5.5 Hz, 1H, H-3'); 4.5 (d, J=5.5 Hz, 2H, H-8); 4.9 (m, 1H, 5'-OH); 5.2 (m, 1H, 3'-OH); 5.8 (d, J=7.4 Hz, 1H, H-5); 6.1 (t, J=6.1 Hz, 1H, H-1'); 6.3 (q, J=0.7 Hz, J=3.2 Hz, 1H, H-9); 6.4 (q, J=1.8 Hz, J=3.2 Hz, 1H, H-10); 7.3 (d, J=7.9 Hz, 1H, H-6); 7.6 (q, J=0.7 Hz, J=1.8 Hz, 1H, H-11); 8 (t, J=5.3 Hz, 1H, NH).

$^{13}$C NMR (75 MHz, DMSO) δ 20.88; 61.34; 70.37; 84.89; 87.89; 94.41; 107.24; 110.48; 125.59; 129.26; 140.23; 142.24; 151.75; 154.92; 163.10.

The 4-N-furfuryl-2'-deoxycytidine (FIG. 1 II) (2) (7.51 mg; 2.45 mmol) was diluted in 1M HCl 20 ml aqueous solution and mixture was refluxed for one hour to received yellow colour of the mixture. Next, the mixture was neutralised by 1M aqueous solution of sodium hydroxide. The reaction mixture was evaporated to dryness under reduced pressure. The 4-N-furfurylcytosine (3) was purified on column with silanised silica gel and was eluted by 0.1% solution methanol in warm water (40-45° C.). White powder was obtained with yield 90%. The TLC analysis showed that it was a complete reaction: $R_f(A)$ 0.54.

ES-MS: ES$^-$ m/z 190 (M–H$^+$), 191 (M); ES$^+$ m/z 192 (M+H$^+$), 214 (M+K$^+$).

$^1$H NMR (300 MHz, DMSO) δ 4.5 (d, J=5.4 Hz, 2H, H-8); 5.6 (d, J=7.1 Hz, 1H, H-5); 6.3 (q, J=0.73 Hz, J=3.2 Hz, H1, H-9); 6.4 (q, J=1.9 Hz, J=3.2 Hz, 1H, H-10); 7.2 (d, J=7.1, 1H, H-6), 7.6 (q, J=0.73 Hz, J=1.9 Hz, 1H, H-11); 7.9 (t, J=5.6 HZ, 1H, NH); 10.3, (a, 1H, NH).

$^{13}$C NMR (75 MHz, DMSO) δ 20.88; 93.10; 107.16; 110.46; 125.59; 129.27; 141.82; 151.96; 156.55; 164.29.

The 4-N-furfurylcytosine was dissolved in minimum amount of water, in which this compound is soluble. This mixture was left overnight in ambient temperature. The received crystals were filtered and washed by dichloromethane and dried under reduced pressure overnight.

To the reaction flask with 40 g cytosine (0.36 mol) 190 ml furfurylamine (6 mol), the same amount of water and 5.67 g catalyst ammonium chloride (0.3 mol) was added. The mixture was heated till boiling within 48-96 h. After cooling, the mixture was extracted with dichloromethane (ca. 300 ml). The organic layer was filtrated to isolate the product. The raw product was crystallized and 61.196 g of pure product was obtained with yield 89%.

Example 2

The Chemical Synthesis of 4-N-furfurylcytosine in One Step

The aim of synthesis was to obtain 4-N-furfurylcytosine. This product was obtained in one step reaction, in which cytosine was heated in water solution of furfurylamine. The following reagents were used: cytosine (Fluka), furfurylamine (Fluka). Thin layer chromatography (TLC) was performed on plates of Silicagel 60 F$_{254}$ (Merck). To detect the UV-absorbance short-ware ultraviolet light (254 nm) was used. $^1$H-NMR and $^{13}$C-NMR spectra were recorded using a Varian 300 MHz spectrometer. Mass spectra (EMS) were measured with ES-MS ZQ apparatus (Waters).

4-N-furfurylcytosine (2)

To the reaction flask with 40 g cytosine (0.36 mol), 190 ml furfurylamine (6 mol) (FIG. 1 IV and V), the same amount of water and 5.67 g catalyst ammonium chloride (0.3 mol) was added. The mixture was heated till boiling within 48-96 h. After cooling, the mixture was extracted with dichloromethane (ca. 300 ml). The organic layer was filtered to isolate the product. The raw product was crystallized and 61.196 g of pure product was obtained with yield 89%.

Example 3

Purification of the Product

The main product (4-N-furfurylcytosine) shown low solubility in all kind of solvents, the best solubility was observed in water, and it increases with temperature. In this reason, purify on the column was performed in warm water (40-45° C.). The column was referred by aluminium foil, because the decrease temperature of water was carried out to precipitate of the product on the gel. The purification of the product was performed two times, because acid degradation of ribose gave a lot of byproducts, obstructed purification. The main product was eluted in 0.1% warm water solution of methanol. When the temperature of solvent was higher than 45° C., the product could elute earlier. The 4-N-furfurylcytosine was crystallized in water, gave colorless crystals, which form thin needles.

Example 4

Effect of 4-N-furfurylcytosine on the Morphology of Late Passage Cells after 7 and 14 Days The role of FC in cytotoxicity (induction of apoptosis, gene expression) has been studied. The action of FC appears to be novel and we want to investigate the potential function as a chemotherapeutic agent.

Figure 2A:
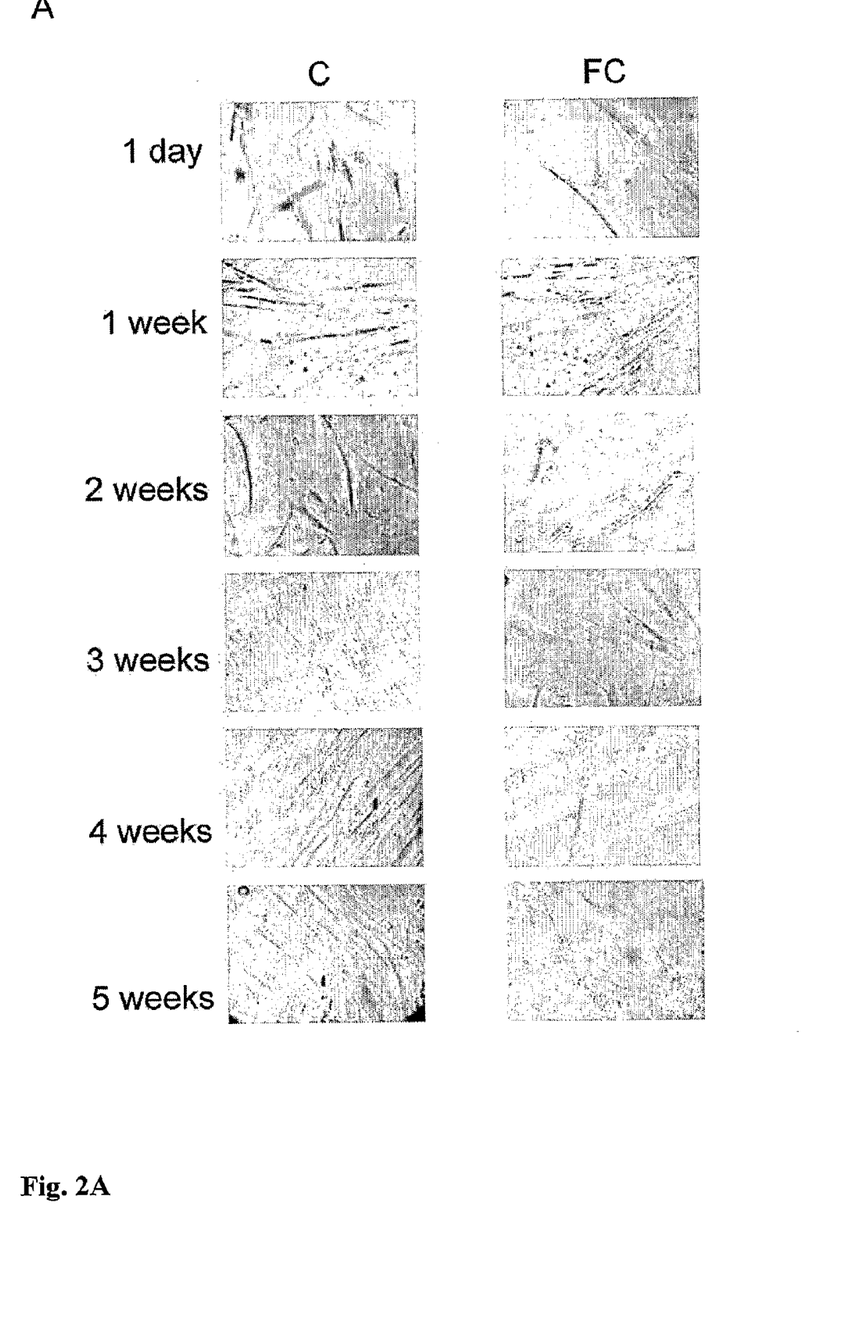

Initially, we assessed the cytotoxic effect of FC on the fibroblast cell viability cultured with 100 μM FC for 5 weeks. We observed decreases in cell viability just after 3 weeks, the control culture untreated with FC was growing well. It was observed much less living cells and after 5 weeks they are clearly death (FIG. 2A).

Figure 2B:
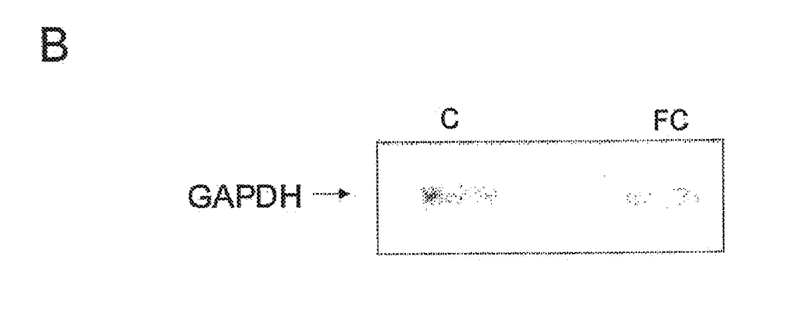
Figure 2C:
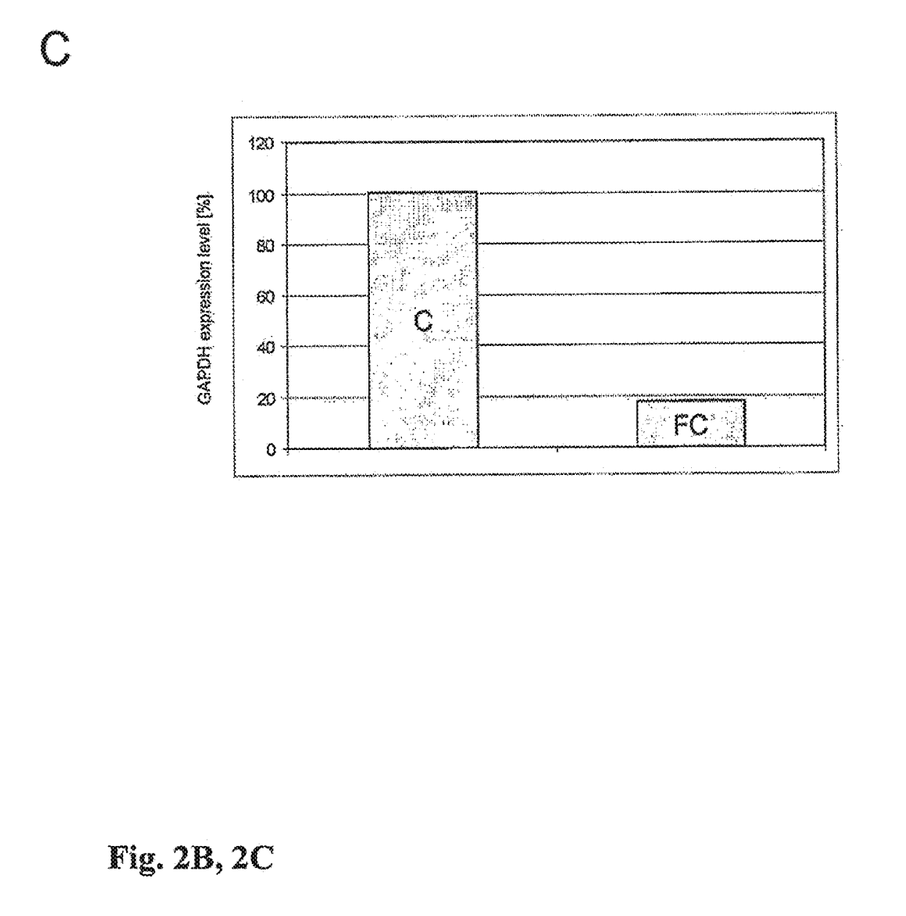

To confirm this observation total RNA was isolated and RT/PCR was perform to analyzed total GAPDH gene expression as a result of condition of cells survival (FIG. 2B) The phosphoimager analysis was performed to determined differences in GAPDH expression in fibroblast cells. We observed that it is 72% lower in FC treated cells in comparison to the control (FIG. 2C).

Figure 3:
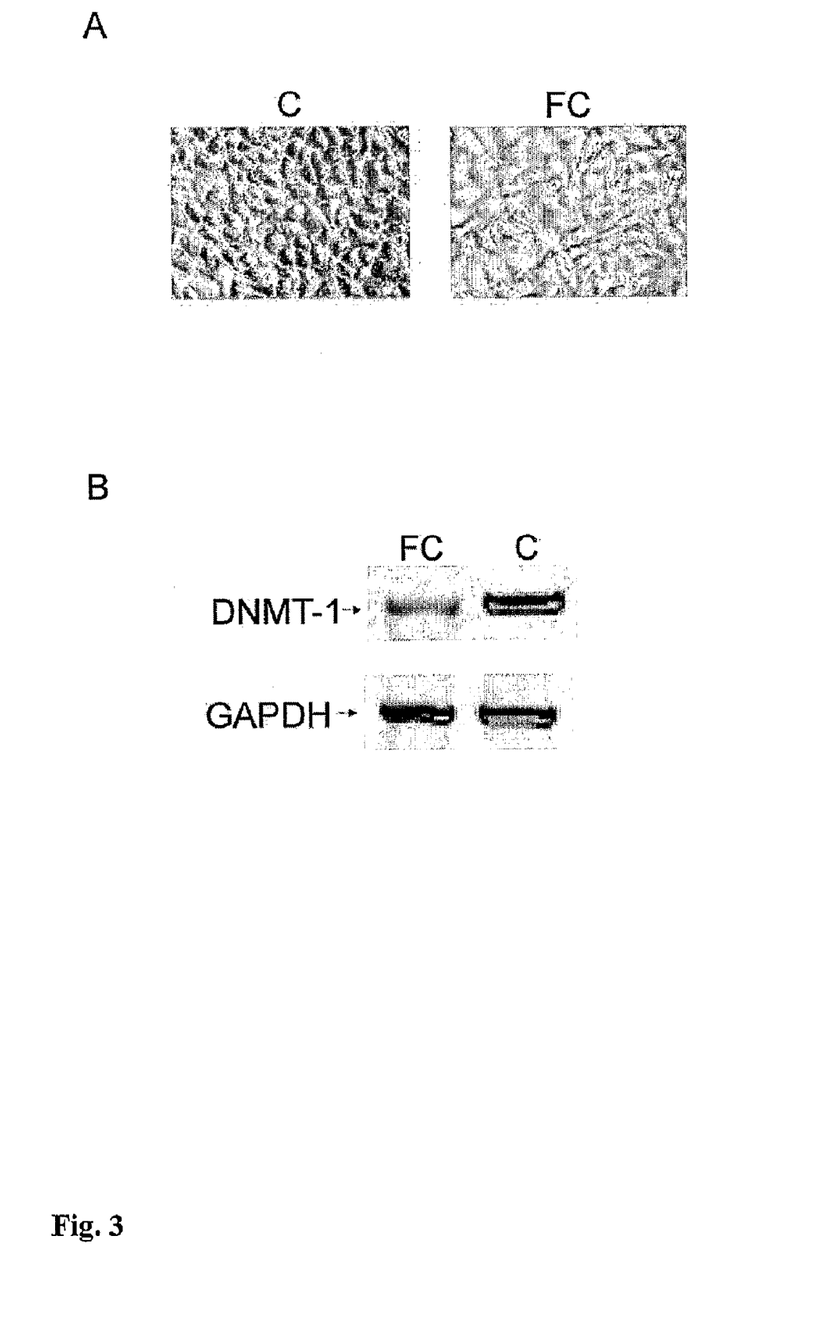
FIG. 3 presents an effect of furfurylcytosine (FC) on DNMT-1 gene expression in HeLa cells.

In other test, we have analyzed influence of FC on the specific gene expression. In this case it was DNMT-1. Effect of FC on DNMT-1 expression was check in HeLa cells after 24 hours (FIG. 3A). It was observed increase of DNMT-1 expression in cells treated with FC in comparison to the untreated control samples control HeLa cells. GAPDH expression level was stable and similar (FIG. 3B).

Cell Culture

HeLa and fibroblast cells are routinely maintained in this laboratory. Fibroblast cells were grown in Optimem medium supplemented with 10% fetal calf serum and antibiotics, HeLa cells were grown in RPMI 1640 supplemented with 10% fetal calf serum and antibiotics (penicillin 100 U/ml and streptomycin 100 ug/ml). All cell lines were incubated in a humidified atmosphere with 5% $CO_2$ in air at 37° C.

There $1 \times 10^6$ cells on 6-well plates were used to study the cytotoxicity area of FC on cell growth in the presence or absence of FC.

RNA Isolation and PCR Analysis

Total RNA from cells was isolated using TRIZOL reagent (Invitrogen). Samples for analyses of gene expression were prepared from cultured Hela and fibroblast cells Aliquots ($1 \times 10^6$ cells) were removed and homogenized in TRIZOL reagent (Invitrogen). Total RNA was then chloroform extracted and precipitated using iso-propanol and ethanol. Reverse transcription was carried out using: 2 μg RNA, random primer and RevertAid™ H Minus M-MuLV reverse transcriptase (Fermentas) according to the manufactures instructions. The resultant cDNA was amplified with primers complementary to the glyceraldehyde-3-phosphate dehydrogenase, GAPDH (G1: GGGTGGAGCCAAACGGGTC, G2: GGAGTTGCTGTTGAAGTCGCA) PCR reaction was initiated with denaturation at 94° C. for 2 min, annealing at 55° C. for 1 min, extension at 72° C. for 30 sec, followed by 30 cycles. Equal volumes of amplified products were electrophoresed on 1 agarose gel and stained with ethidium bromide.

Differences in expression level were determined using Phosphoimager and ImageQant program.

Example 5

Chemical Synthesis of 4-N-furfuryl-5-methylcytosine

Figure 4:
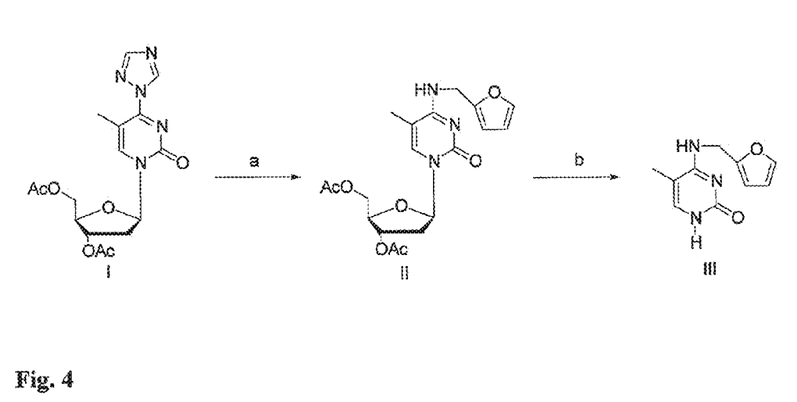
FIG. 4 presents synthesis of 4-N-furfuryl-5-methylcytosine (III), wherein I is a 4-(1,2,4-triazole-1-yl)-5-methyl-2-pirymidon-1-yl-β-D-3',5'-di-O-acetyl-2'-deoxyribofuranoside and II is a 4-N-furfuryl-5-methyl-2'-deoxycytidine, (a) is a furfurylamine (1.5 equiv.), acetonitrile, 50° C., 2 h, and (b) HCl, methanol, water, Δ, 4 h.
Figure 5:
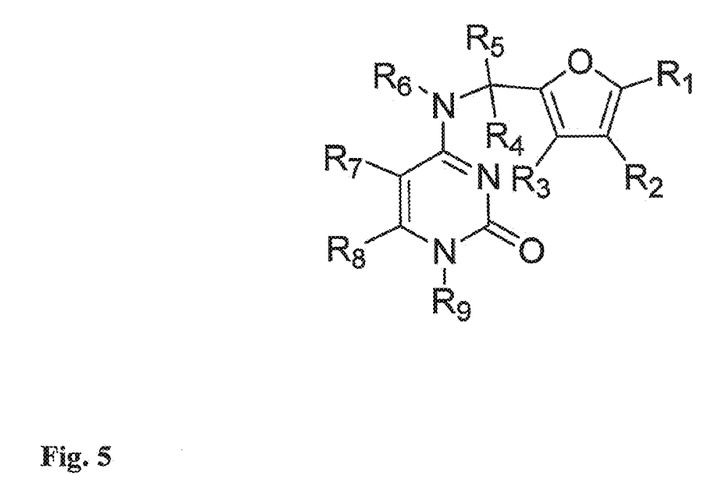

The chemical synthesis of 4-N-furfuryl-5-methylcytosine (III) was achieved in three steps (FIG. 4).

The first step was the synthesis of 4-(1,2,4-triazole-1-yl)-5-methyl-2-pirymidon-1-yl-β-D-3',5'-di-O-acetyl-2'-deoxyribofuranoside according to the procedure described by Matteucci et al. [Matteucci M. D., Webb T. R. "Hybridization triggered cross-linking of deoxyoligonucleotides" (1986) Nucleic Acids Research, 14, 19, 7661-7674].

The second step was the reaction of furfuryloamine with 4-(1,2,4-triazole-1-yl)-5-methyl-2-pirymidon-1-yl-β-D-3', 5'-di-O-acetyl-2' deoxyribofuranoside.

The third step was to obtain 4-N-furfuryl-5-methylcytosine via acid hydrolysis of the N-glicoside bond using an aqueous solution of an inorganic acid. When the reaction ended the acid was neutralised by methanol solution of sodium hydroxide, solvents were evaporated. After re-dissolving in water the product was extracted by n-butanol, which next was evaporated to dryness, giving white-yellow precipitate.

4-N-furfuryl-5-methylo-2'-deoxycytidine (II)

To solution of 4-(1,2,4-triazole-1-yl)-5-methyl-2-pirymidon-1-yl-β-D-3',5'-di-O-acetyl-2' deoxyribofuranoside (I) (388 mg, 1.325 mmol) in anhydrous acetonitrile (15 ml) furfurylamine (0.176 ml 1.987 mmol) was added. The reaction flask was closed and kept at 50° C. for 2 hours. Product in the form of beige residuum was filtered. To remove the acetyl groups, the residuum was inserted into the reaction flask with methanol (15 ml) and 32% aqueous ammonia (15 ml). The mixture was heated till boiling for an hour. Than the solvents were evaporated under reduced pressure. The dry residue was extracted with methylene chloride (20 ml) and water (3×20 ml). The water layer (with product) was evaporated. White foam was obtained with yield 94%.

TLC analysis showed that it was a complete reaction: Rf (AcOEt: MeOH, 6:4) 0.5.

ES-MS: $ES^+$ m/z 322 $[M+H]^+$, 360 $[M+K]^+$.

$^1$H-NMR: (300 MHz, DMSO) δ 1.8 (s, 3H, $CH_3$); 1.9 (m, 1H, H-2'); 2 (m, 1H, H-2"); 3.5 (d, J=2.4 Hz, 2H, H-5'); 3.7 (q, J=3.8 Hz, J=6.7 Hz, 1H, H-4'); 4.2 (t, J=2.9 Hz, 1H, H-3'); 4.5 (d, J=5.8 Hz, 2H, H-8); 5.0 (m, 1H, 5'-OH); 5.1 (m, 1H, 3'-OH); 6.1 (t, J=5.8 Hz, 1H, H-1'); 6.2 (d, J=2.9 Hz, 1H, H-9); 6.3 (m, 1H, H-10); 7.3 (m, 1H, H-11); 7.8 (s, 1H, H-6); 8 (m, 1H, NH).

4-N-furfuryl-5-methylcytosine (III)

4-N-furfuryl-5-methyl-2'-deoxycytidine (399 mg, 1.245 mmol) was dissolved in the mixture of water (10 ml) and methanol (5 ml), to which concentrated aqueous HCL acid was added (0.31 ml, 3.736 mmol). The mixture was heated till boiling for ca. 4 hours, controlling the reaction progress on the TLC plate. Than the acid was neutralised using 1 M methanol solution of NaOH, and than the solvents were evaporated. The dry pozostałość was separated into water (10 ml) and n-butanol (3×10 ml), and than to the organic layer the active carbon was added (0.300 g). The carbon was filtered and the filtrate was evaporated till dryness obtaining white-yellow residuum with yield 74%. The reaction progress was made on the TLC plate, covered by silan gel in the eluent B: Rf (AcOEt: MeOH 6:4) 0.4 lub C: Rf (aceton:water 15:1) 0.7.

ESI-MS: $ES^+$ m/z 206 $[M+H]^+$, 238 $[M+H+MeOH]^+$, 244 $[M+K]^+$.

$^1$H-NMR (300 MHz, $D_2O$) δ 1.3 (s, 3H, $CH_3$); 4.6 (s, 2H, H-8); 6.2 (m, 1H, H-9); 6.3 (m, 1H, H-10); 7.3 (m, 1H, H-11); 7.4 (s, 1H, H-6).

CONCLUSIONS

These results suggested that FC induced cytotoxic effect in fibroblast cells cultured long time (5 weeks). This observation appears after 3 week of cultured cells and is deepened. To explain this effect Hela cells were treated FC to analyze specific gene expression.

We observed that FC inhibits expression of DNA methyltransferase (DNMT-1) in HeLa cells in comparison to the control. It is essential for cytosine 5' methylation of CpG dinucleotides within and around genes exerts a major influence on transcription. DNA methylation can be causal for transcriptional silencing. This enzyme plays an essential role in mammalian cell regulation. Alteration in DNA methylation pattern can promote tumorgenesis and predispose genes to mutational events.

FC, the small molecule compound can block expression of DNMT-1 and be apply as potent inhibitor with significant potential for further drug development.

extracted with dichloromethane, whereafter the organic phase is filtered in order to isolate the product and the raw product is then crystallised and wherein the synthesis of 4-N-furfurylcytosine and/or its derivatives consists of three stages, during the first stage 4-N-p-toluenesulfonyl-2'-deoxycytidine is synthesized, during the second stage the furfurylamine reacts with the 4-N-p-tosyl-2'-deoxycytidine, and the third stage consists of the formation of 4-N-furfurylcytosine and/or its derivatives through the degradation of the N-glycoside bond with an aqueous solution of an acid, wherein the degradation of the N-glycoside bond during the third stage is performed using an aqueous solution of an inorganic acid at a pH of 3-3.5; following the formation of 4-N-furfurylcytosine and/or its derivatives, the acid is evaporated off or neutralised with aqueous sodium hydroxide, and the salt formed is separated on a chromatography column and the chromatographic purification is performed at least twice, where the chief product is eluted with an aqueous solution of methanol, where the salt formed is separated on a chromatography column at a temperature of 40-45° C., and the main product is eluted with a 0.1% aqueous solution of methanol and the 4-N-furfurylcytosine is crystallized in water and colourless, needle-shaped crystals are obtained.

The invention claimed is:

1. A cosmetic or pharmaceutical composition comprising 4-N-furfurylcytosine and/or its derivatives, of the general formula wherein:
$R_1$, $R_2$, $R_3$=H, alkyl, alkenyl, alkinyl, hydroxyalkyl or aryl
$R_4$, $R_5$, $R_6$=H or alkyl
$R_7$, $R_8$=H, $CH_3$, alkyl, alkenyl, alkinyl, or hydroxyalkyl
$R_9$=H, D-2-deoxyriboside, D-riboside, or tetrahydropyranyl.

2. A composition according claim 1, characterised in that the 4-N-furfurylcytosine and/or its derivatives content in the composition is up to 2%.

3. A composition according to claim 1, characterised in that the composition contains 4-N-furfurylcytosine and/or its derivatives the synthesis of which encompasses a reaction stage in which an aqueous solution of cytosine is supplemented with furfurylamines and a catalyst ammonium chloride, wherein the molar ratio of cytosine to furfurylamine to the catalyst, ammonium chloride is 0.36:6:0.3, whereafter the mixture is brought to boiling for 48 to 96 hours, cooled and 4. A method of using a cosmetic composition that comprises 4-N-furfurylcytosine and/or its derivatives, of a general formula wherein:

$R_1, R_2, R_3$=H, alkyl, alkenyl, alkinyl, hydroxyalkyl or aryl $R_4, R_5, R_6$=H or alkyl $R_7, R_8$=H, $CH_3$, alkyl, alkenyl, alkinyl, or hydroxyalkyl $R_9$=H, D-2-deoxyriboside, D-riboside, or tetrahydropyranyl comprising:

applying the cosmetic composition to skin.

5. The method according to claim 4, characterised in that the cosmetic composition that is applied to the skin includes up to 2% of the 4-N-furfurylcytosine and/or its derivatives.

6. The method according to claim 4, characterised in that the 4-N-furfurylcytosine and/or its derivatives included in the cosmetic composition that is applied to the skin is obtained in a reaction stage in which an aqueous solution of cytosine is supplemented with furfurylamines and a catalyst ammonium chloride, wherein the molar ratio of cytosine to furfurylamine to the catalyst, ammonium chloride is 0.36:6:0.3, whereafter the mixture is brought to boiling for 48 to 96 hours, cooled and extracted with dichloromethane, whereafter the organic phase is filtered in order to isolate the product and the raw product is then crystallised and wherein the synthesis of 4-N-furfurylcytosine and/or its derivatives consists of three stages, during the first stage 4-N-p-toluenesulfonyl-2'-deoxycytidine is synthesized, during the second stage the furfurylamine reacts with the 4-N-p-tosyl-2'-deoxycytidine, and the third stage consists of the formation of 4-N-furfurylcytosine and/or its derivatives through the degradation of the N-glycoside bond with an aqueous solution of an acid, wherein the degradation of the N-glycoside bond during the third stage is performed using an aqueous solution of an inorganic acid at a pH of 3-3.5; following the formation of 4-N-furfurylcytosine and/or its derivatives, the acid is evaporated off or neutralised with aqueous sodium hydroxide, and the salt formed is separated on a chromatography column and the chromatographic purification is performed at least twice, where the chief product is eluted with an aqueous solution of methanol, where the salt formed is separated on a chromatography column at a temperature of 40-45° C., and the main product is eluted with a 0.1% aqueous solution of methanol and the 4-N-furfurylcytosine is crystallized in water and colourless, needle-shaped crystals are obtained.

7. The composition recited in claim 1, wherein the composition is a cosmetic composition that is operative to be applied to skin.

\* \* \* \* \*